(12) United States Patent  
Liddicoat

(10) Patent No.: US 7,300,463 B2  
(45) Date of Patent: Nov. 27, 2007

(54) FIXATION BAND FOR AFFIXING A PROSTHETIC HEART VALVE TO TISSUE

(75) Inventor: John R. Liddicoat, Sewickley, PA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/038,020

(22) Filed: Jan. 18, 2005

(65) Prior Publication Data

US 2005/0261765 A1    Nov. 24, 2005

Related U.S. Application Data

(63) Continuation of application No. 09/949,061, filed on Sep. 7, 2001, now Pat. No. 6,846,325.

(60) Provisional application No. 60/230,756, filed on Sep. 7, 2000.

(51) Int. Cl.  
*A61F 2/24*    (2006.01)

(52) U.S. Cl. ..................................................... 623/2.4

(58) Field of Classification Search ................ 623/2.38, 623/2.4, 2.41  
See application file for complete search history.

(56) References Cited

U.S. PATENT DOCUMENTS

| 3,996,623 A | 12/1976 | Kaster |
| 4,506,394 A | 3/1985 | Bedard |
| 5,843,179 A | 12/1998 | Vanney et al. |
| 6,287,339 B1 | 9/2001 | Vazquez et al. |
| 6,419,696 B1 | 7/2002 | Ortiz et al. |

FOREIGN PATENT DOCUMENTS

| WO | WO 89/00841 | 2/1989 |
| WO | WO 00/44313 | 8/2000 |

*Primary Examiner*—William H. Matthews  
(74) *Attorney, Agent, or Firm*—Mike Jaro; Jeffrey J. Hohenshell

(57) ABSTRACT

A fixation band has a tubular frame and a tube, wherein the tubular frame comprises longitudinally-extending members having a hook on its distal end and fixation means on its proximal end. The tubular frame preferably comprises a laterally-extending member for stabilization. The tube is positioned inside longitudinally-extending members and a sewing cuff is formed in the tube distal to the distalmost end of the longitudinally-extending members. A standard prosthetic valve can be secured to the fixation band by suturing the prosthetic valve's sewing cuff to the fixation band's sewing cuff and the prosthetic valve can be advanced to a valve seat. By pulling the tubular frame proximally, the hooks pass into surrounding tissue so that the fixation band and prosthetic valve are fixed against proximal movement. The fixation means then secure the fixation band to the surrounding tissue so that the prosthetic valve is fixed against distal movement.

10 Claims, 8 Drawing Sheets

FIXATION BAND FOR AFFIXING A PROSTHETIC HEART VALVE TO TISSUE

Reference To Pending Prior Patent Application

This is a continuation of pending prior U.S. patent application Ser. No. 09/949,061, filed Sep. 07, 2001 now U.S. Pat. No. 6,846,325by John R. Liddicoat for FIXATION BAND FOR AFFIXING A PROSTHETIC HEART VALVE TO TISSUE, which in turn claims benefit of prior U.S. Provisional Patent Application Ser. No. 60/230,756, filed Sep. 07, 2000 by John R. Liddicoat for DEVICE AND METHODS FOR THE SUTURELESS IMPLANTATION OF A HEART VALVE. The above-identified patent applications are hereby incorporated herein by reference.

FIELD OF THE INVENTION

This invention relates to surgical apparatus in general, and more particularly to prosthetic heart valves.

BACKGROUND OF THE INVENTION

The human heart consists of four chambers: the right atrium for receiving blood from systemic circulation; the right ventricle for receiving blood from the right atrium and pumping it to the lungs; the left atrium for receiving oxygenated blood from the lungs; and the left ventricle for receiving oxygenated blood from the left atrium and pumping it to systemic circulation.

The human heart also consists of four valves: the tricuspid valve located between the right atrium and the right ventricle; the pulmonary valve located at the output of the right ventricle; the mitral valve located between the left atrium and the left ventricle; and the aortic valve located at the output of the left ventricle.

In some circumstances (e.g., a birth defect, disease, etc.) a natural heart valve may need to be replaced by a prosthetic heart valve. In this situation, sometimes referred to as "on pump" surgery, the patient must be placed on a heart-lung machine and the heart stopped while the defective heart valve is removed and the prosthetic heart valve installed through a major incision made in the wall of the heart. The prosthetic heart valve is typically sutured in place at the annulus, or seat, of the natural heart valve using a sewing cuff disposed about the circular periphery of the prosthetic heart valve.

While such surgery is typically successful, it is also highly traumatic to the body and the use of the heart-lung machine may raise issues of subtle mental impairment in the near term following surgery.

In view of the trauma associated with a major coronary wall incision and possible subtle mental impairment which may be associated with the use of a heart-lung machine, it has been proposed to effect valve replacement without placing the patient on a heart-lung machine and stopping the heart. See, for example, PCT Patent Application No. PCT/US00/02126, filed Jan. 27, 2000 by Gregory Lambrecht et al. for CARDIAC VALVE PROCEDURE METHODS AND DEVICES, published Aug. 3, 2000 as PCT Patent Publication No. WO 00/44313. This type of surgery is sometimes referred to as "off-pump", or "beating heart", surgery.

It has been recognized that if a heart valve is to be replaced with "off-pump", "beating heart" surgery, the incisions made into the vascular system should be as small as possible. However, this can make it difficult to secure the prosthetic heart valve in place, since the prosthetic heart valve is typically sutured to the annulus, or seat, of the natural heart valve, and since suturing (including knot tying) can be difficult to effect through small incisions. This can be particularly true where the incisions may be made into the vascular system at a location remote from the valve seat, e.g., in the superior vena cava in the case of the tricuspid valve, or in the pulmonary artery in the case of the pulmonary valve, or the pulmonary veins in the case of the mitral valve, or the aorta in the case of the aortic valve.

SUMMARY OF THE INVENTION

As a result, one object of the present invention is to provide novel apparatus for quickly, easily and conveniently affixing a prosthetic heart valve in position within the heart.

Another object of the present invention is to provide a novel fixation band for affixing a prosthetic heart valve in position within the heart.

And another object of the present invention is to provide a novel method for affixing a prosthetic heart valve in position within the heart.

These and other objects of the present invention are addressed by the provision and use of a novel fixation band for affixing a prosthetic heart valve in position within the heart.

In one preferred form of the invention, the fixation band generally comprises a tubular frame having a distal end and a proximal end, and a tube having a distal end and a proximal end. The tubular frame comprises a plurality of longitudinally-extending members each having a hook on its distal end and fixation means on its proximal end. The tubular frame also comprises at least one laterally-extending member for stabilizing the longitudinally-extending members relative to one another so as to form the complete tubular frame. The tube is positioned inside the longitudinally-extending members, with the distal end of the tube being everted back over the aforementioned hooks. A sewing cuff is formed in the tube distal to the distalmost end of the longitudinally-extending members.

In use, a standard prosthetic valve is secured to the distal end of the fixation band by suturing the prosthetic valve's sewing cuff to the fixation band's sewing cuff. Next, the prosthetic valve, with fixation band attached, is advanced to the valve's seat. Then the fixation band's tubular frame is pulled proximally slightly. This action causes the ends of the hooks to pass through the side wall of the everted tube and into the surrounding tissue at the valve's seat, whereby the fixation band, and hence the prosthetic valve, will be fixed against further proximal movement. Next, the fixation band's fixation means are deployed so as to secure the proximal end of the fixation band to the surrounding tissue, whereby the fixation band, and hence the prosthetic valve, will be fixed against distal movement.

In one form of the invention, the fixation means may be deployed by bending them radially outwardly so that they engage the surrounding tissue.

In another form of the present invention, the fixation means may be deployed by removing a restraining device, whereby the fixation means will automatically deploy against the surrounding tissue.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIEMENTS

Figure 1:
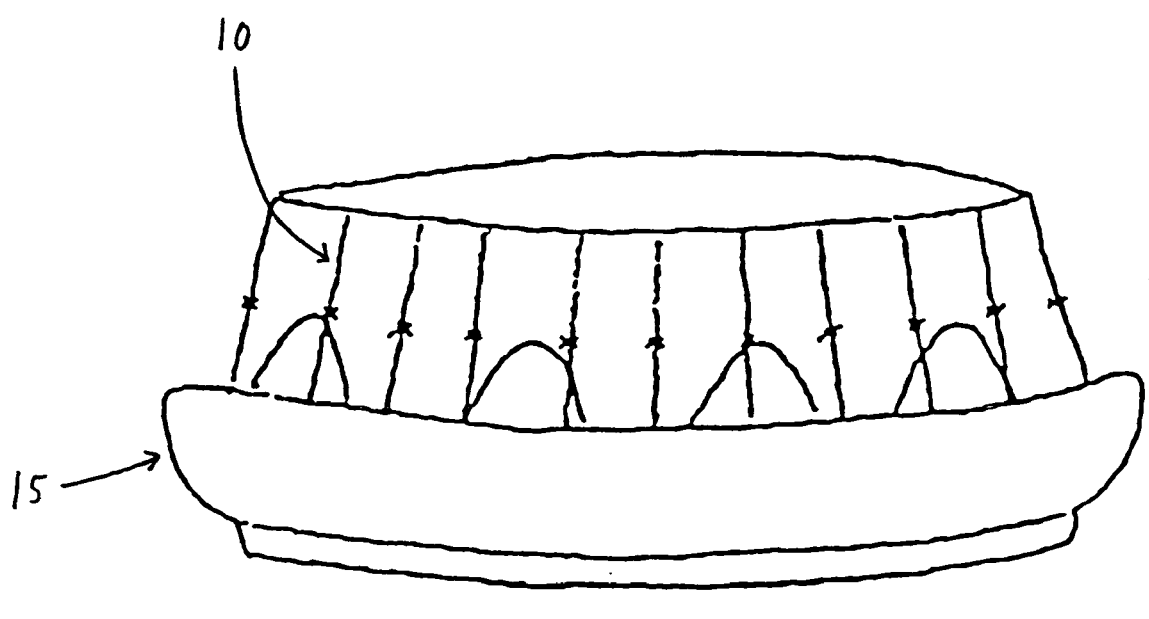
FIG. 1 is a schematic view of a fixation band formed in accordance with the present invention.

Looking first at FIG. 1, there is shown a fixation band 5 which comprises one preferred form of the invention. Fixation band 5 generally comprises a tubular frame 10 and a tube 15.

Figure 2:
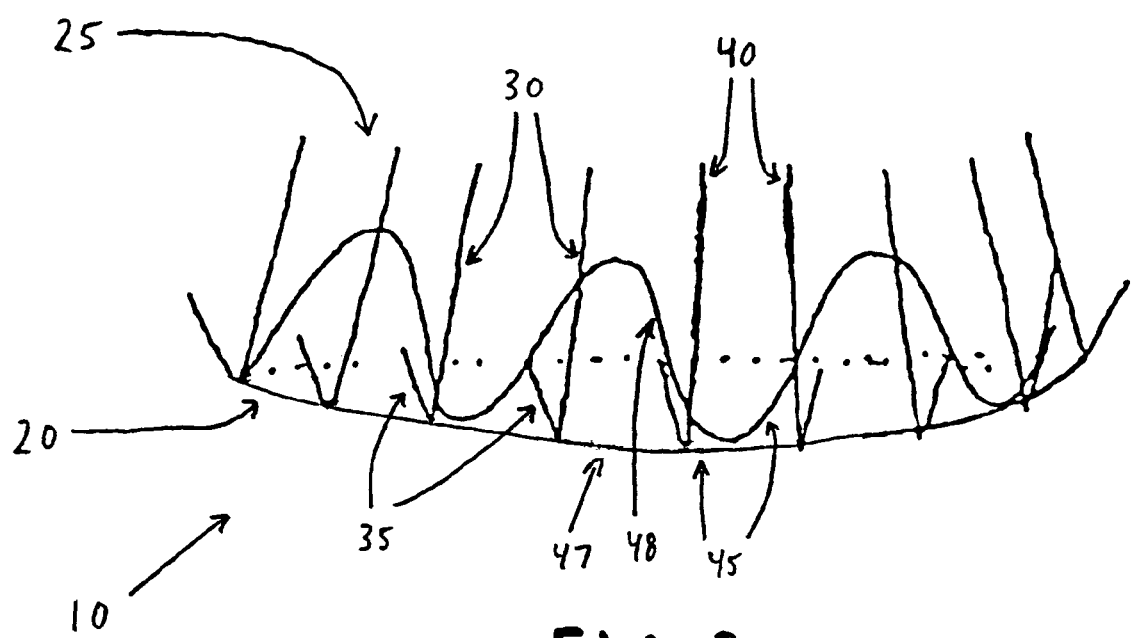
FIG. 2 is a schematic view of the fixation band's tubular frame.

Tubular frame 10 is shown in greater detail in FIG. 2. Tubular frame 10 generally comprises a distal end 20 and a proximal end 25. Tubular frame 10 comprises a plurality of longitudinally-extending members 30 each having a hook 35 on its distal end, and fixation means 40 (discussed in further detail below) on its proximal end. Tubular frame 10 also comprises at least one laterally-extending member 45 for stabilizing the longitudinally-extending members 30 relative to one another so as to form the complete tubular frame. In one form of the invention, each laterally-extending member 45 extends completely around the circumference of the frame, in the manner shown in FIG. 2. Alternatively, a series of separate laterally-extending members 45 may be used to span the circumference of tubular frame 10. Furthermore, in one form of the invention, laterally-extending member 45 may be in the form of a circular hoop, like the hoop of a barrel, such as the laterally-extending member 47 shown in FIG. 2. Alternatively, and/or in addition, laterally-extending member 45 may have a serpentine configuration, such as the laterally-extending member 48 shown in FIG. 2.

Figure 3:
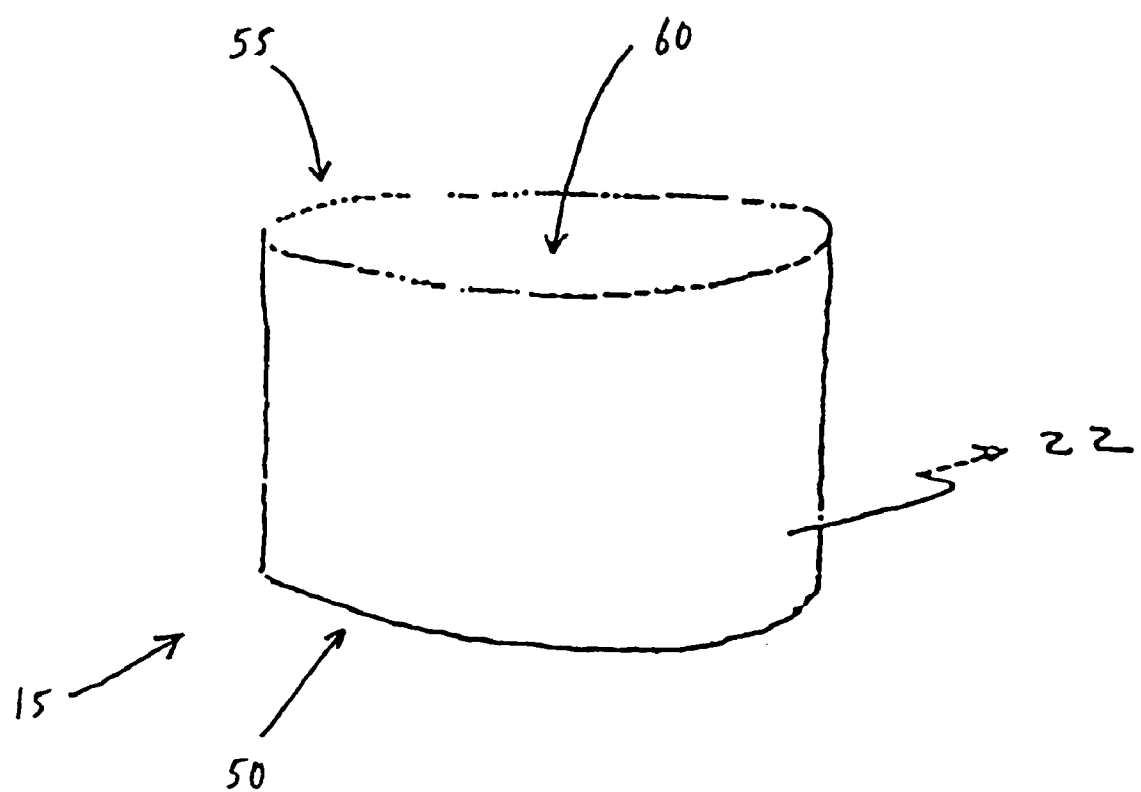
FIG. 3 is a schematic view of the fixation band's tube prior to its assembly with the tubular frame.

Tube 15 is, initially, an ordinary straight tube such as is shown in FIG. 3, i.e., it is a hollow structure having a distal end 50, a proximal end 55 and a central lumen 60 extending therebetween. Tube 15 is preferably formed out of material which is easily incorporated in tissue, e.g., Dacron polyester or the like. Tube 15 may be vertically pleated or elastic, whereby to allow the material to stretch radially.

Figure 4:
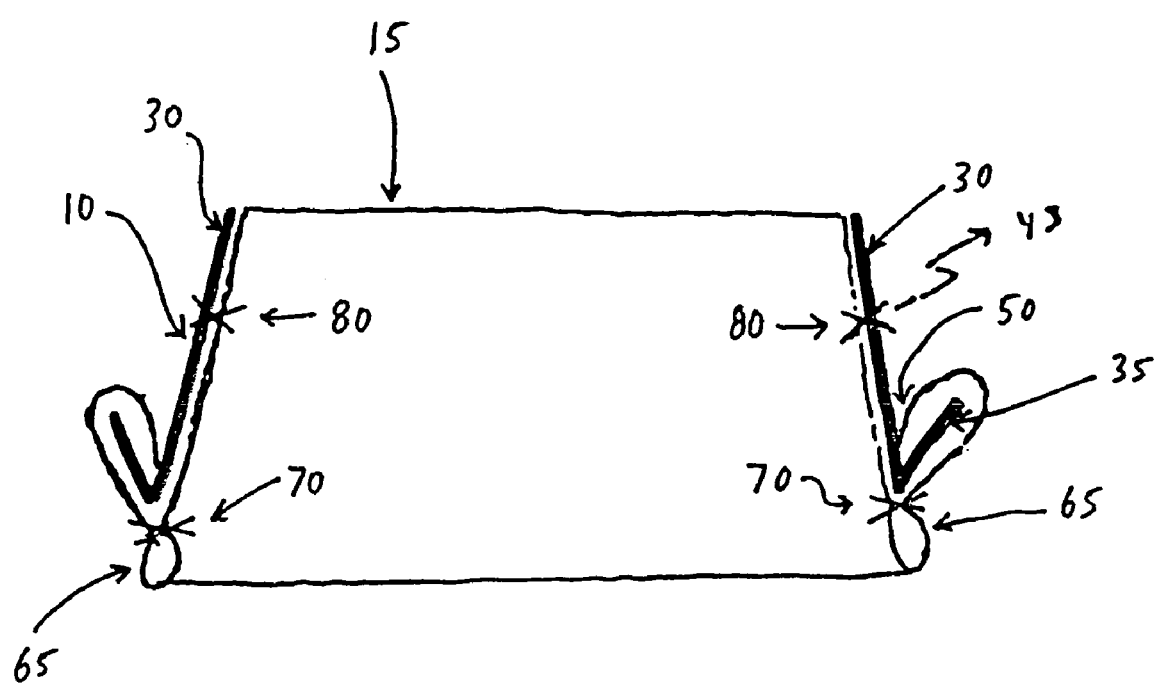
FIG. 4 is a schematic view of the complete fixation band shown in FIG. 1.

Tube 15 is mounted to tubular frame 10 as follows. First, the distal end 50 of tube 15 is passed, distally, down the interior of tubular frame 10. Then the distal end 50 of tube 15 is everted (FIG. 4) so as to fold it back over, and cover, the hooks 35 of longitudinally-extending members 30.

As this is done, a sewing cuff 65 is formed in tube 15 distal to the distalmost end of longitudinally-extending members 30. Tube 15 may then be secured in this position, e.g., with sutures 70 maintaining sewing cuff 65 and with sutures 80 holding tube 15 to longitudinally-extending members 30.

Figure 5:
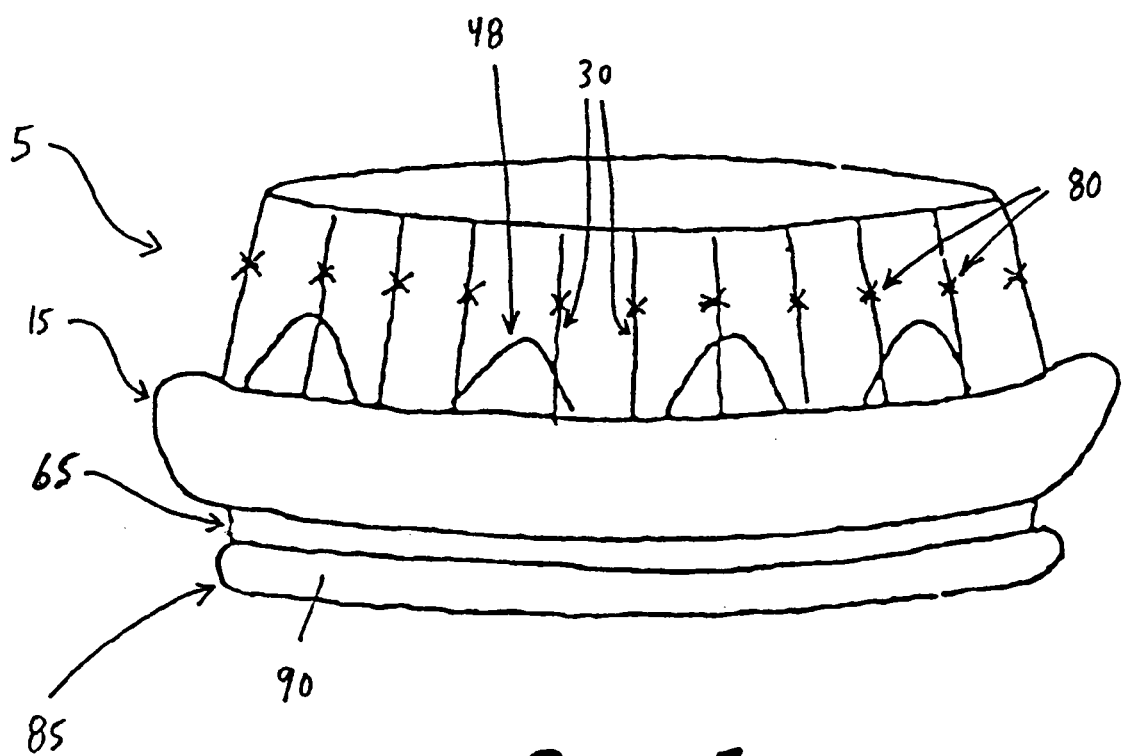
FIG. 5 is a schematic view showing a prosthetic heart valve secured to the fixation band of FIG. 1.
Figure 6:
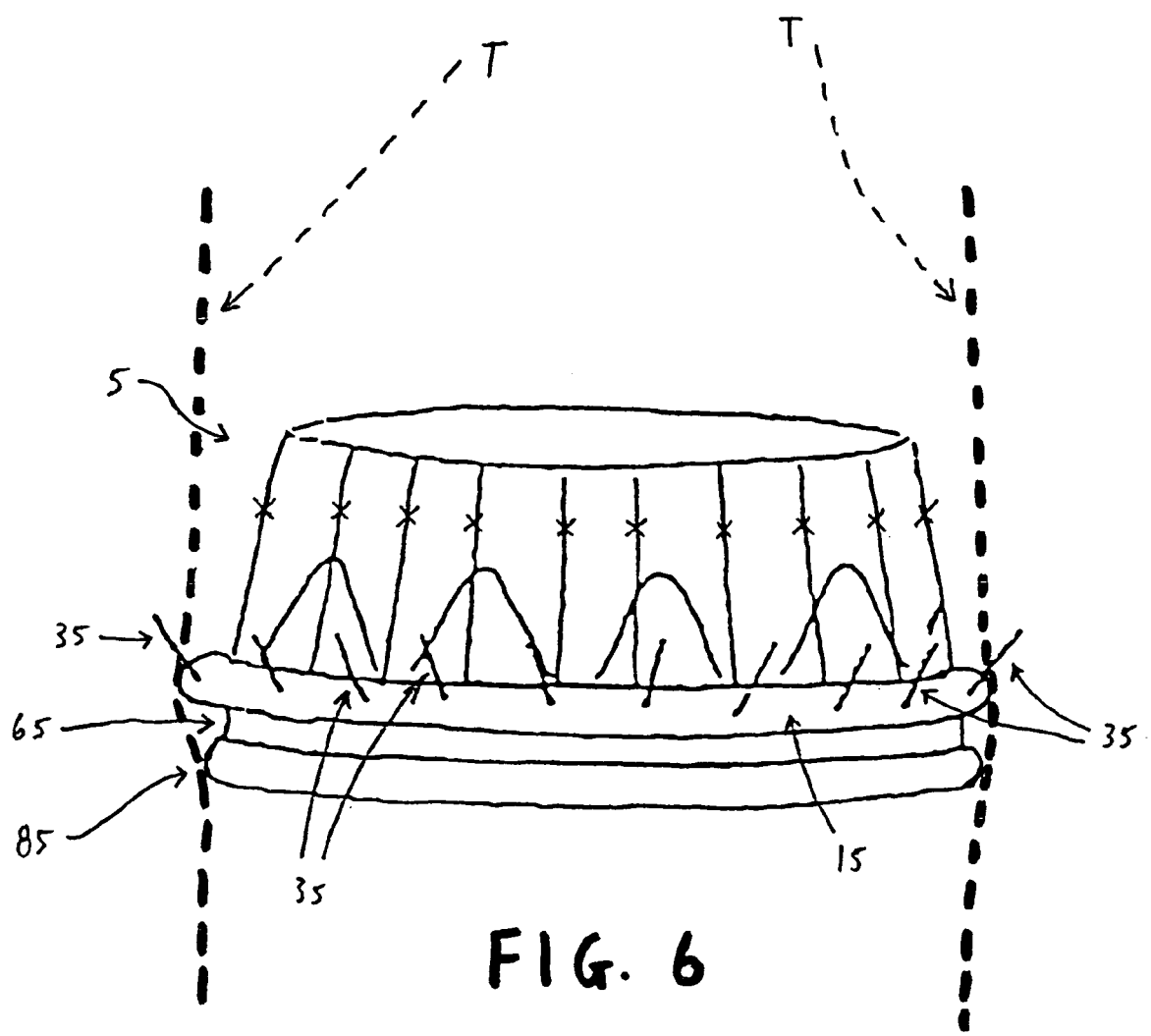
FIG. 6 is a schematic view showing the assembly of FIG. 5 after deployment of the fixation band's distal hooks.
Figure 7:
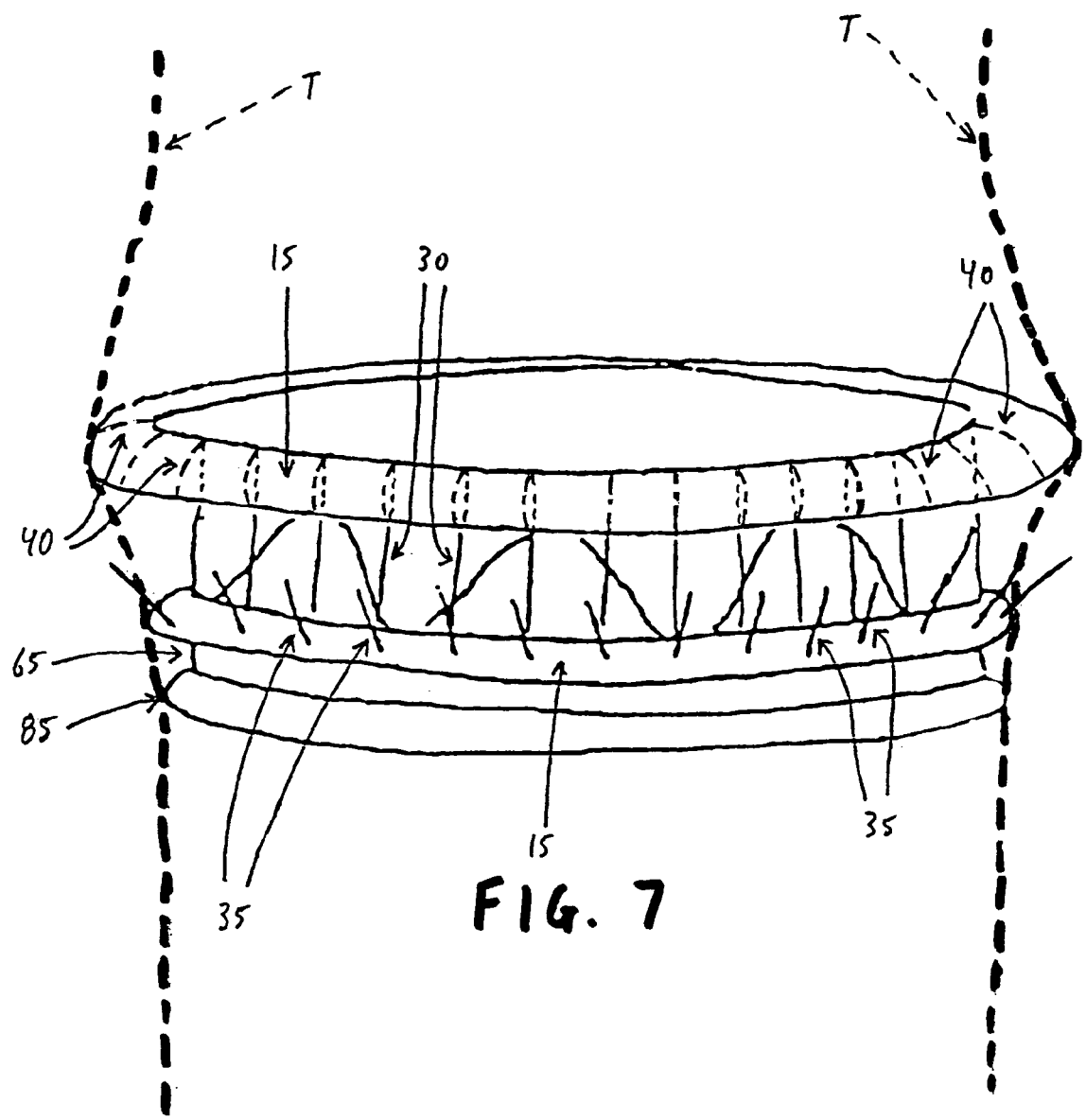
FIG. 7 is a schematic view showing the assembly of FIG. 6 after deployment of the fixation band's proximal fixation means.

In use, a standard prosthetic heart valve 85 (FIG. 5) is secured to the distal end of fixation band 5 by sewing the prosthetic heart valve's sewing cuff 90 to the fixation band's sewing cuff 65. Next, the prosthetic valve 85, with fixation band 5 attached, is advanced to the valve's seat. Then the fixation band's tubular frame 10 is pulled proximally slightly. This action causes the ends of the hooks 35 to pass through the side wall of the everted tube 15 (FIG. 6) and into the surrounding tissue T at the valve's seat, whereby fixation band 5, and hence prosthetic valve 85, will be fixed against further proximal movement. Next, the fixation band's fixation means 40 are deployed (FIG. 7) so as to secure the proximal end of the fixation band to surrounding tissue, whereby the fixation band, and hence the prosthetic valve, will be fixed against distal movement. Where the fixation means 40 are secured to the proximal end of tube 15, the proximal end of tube 15 will follow the curvature of the deploying fixation means 40, such as is shown in FIG. 7. Alternatively, if fixation means 40 are free to move independently outboard relative to the proximal end of tube 40, either because they are not secured to tube 15 or they extend past the proximal end of the tube, fixation means 40 are free to move separately into the surrounding tissue.

In one form of the invention, fixation means 40 may be deployed by bending the proximal ends of longitudinally-extending members 30 outwardly, e.g., with an annular forming tool or a forceps-type device.

Figure 8:
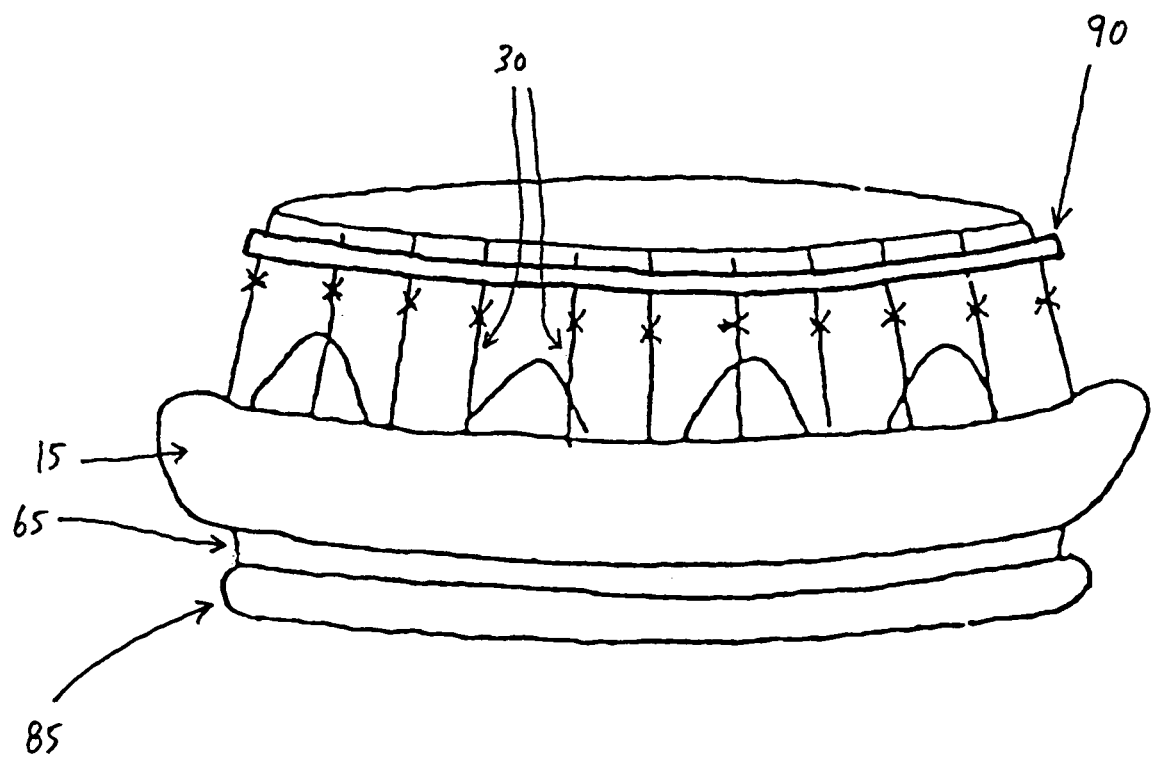
FIG. 8 is a schematic view showing a restraining device for restraining the fixation band's proximal fixation means.

In another form of the invention, fixation means 40 may be deployed by removing a restraining device, e.g., a collar 90 (FIG. 8), whereby fixation means 40 will automatically deploy against the surrounding tissue.

Fixation band 5 may be used to affix prosthetic heart valve 85 to tissue in a conventional on-pump surgical procedure. Alternatively, and more preferably, fixation band 5 may be used to affix prosthetic heart valve 85 to tissue in a beating heart, off-pump surgical procedure. In this case, the assembled heart valve 85 and fixation band 5 are advanced to the intended valve seat by passing the assembly through an appropriate vascular pathway, e.g., in the case of the aortic valve, by passing the assembly down the aorta.

It should be appreciated that various modifications may be made to the preferred embodiments described above without departing from the scope of the present invention. Thus, for example, in the foregoing description, tubular frame 10 is described as being fully assembled (i.e., laterally-extending member 45 is secured to longitudinally-extending member 30) prior to being joined with tube 15 so as to form the complete fixation band 5. However, it should also be appreciated that longitudinally-extending members 30 and/or the laterally-extending member 45 may be secured to tube 15 prior to being joined to one another.

Furthermore, in the foregoing description, tube 15 is described as being, prior to eversion, an ordinary straight tube. However, if desired, tube 15 could be flared outwardly toward its distal end 50 to facilitate eversion over hooks 35, and/or it could include a radially-extending flange at its distal end to facilitate eversion over hooks 35, where the flange may be formed separately from the main body of the tube.

Still other modifications and variations will be apparent to those skilled in the art in view of the present disclosure, and are considered to be within the scope of the present invention.

What is claimed is:

1. A fixation band for implantation and affixing a prosthetic heart valve to tissue, said fixation band comprising:

a tubular body including a proximal end and a distal end, the body comprising a plurality of longitudinally extending members with radially expandable distal ends for securing said fixation band to tissue; and a tube positioned inside said longitudinally extending members, and with a sewing cuff being formed in said tube distal to the distalmost end of said longitudinally extending members so that a prosthetic heart valve will be attached to the fixation band at a position distal from the expandable distal ends of the longitudinally extending members.

2. A fixation band according to claim 1 wherein said plurality of longitudinally extending members comprise at least one hook disposed at a distal end of said body.

3. A fixation band according to claim 1 wherein said plurality of longitudinally extending members comprise fixation means disposed at said proximal end of said body.

4. A fixation band according to claim 3 wherein said fixation means are actuated by bending the same radially outwardly so as to engage the surrounding tissue.

5. A fixation band according to claim 3 wherein said fixation means are adapted to be deployed by removing a restraining device, whereby the fixation means will automatically deploy against the surrounding tissue.

6. A fixation band for implantation and affixing a prosthetic heart valve to tissue, said fixation band comprising:

a tubular frame having a distal end and a proximal end, said tubular frame comprising a plurality of longitudinally-extending members each having a hook on its distal end and fixation means on its proximal end, and at least one laterally-extending member for stabilizing the longitudinally-extending members relative to one another so as to form the complete tubular frame; and a tube positioned inside said longitudinally-extending members, with the distal end of said tube being everted back over said hooks, and with a sewing cuff being formed in said tube distal to the distalmost end of said longitudinally-extending members.

7. A fixation band according to claim 6 wherein said fixation means are actuated by bending the same radially outwardly so as to engage the surrounding tissue.

8. A fixation band according to claim 6 wherein said fixation means are adapted to be deployed by removing a restraining device, whereby the fixation means will automatically deploy against the surrounding tissue.

9. A fixation band according to claim 6 wherein said tube is flared outwardly at said distal end of said tube.

10. A fixation band according to claim 6 wherein said tube comprises a radially-extending flange at its distal end.

* * * * *